United States Patent
Schwartz et al.

(10) Patent No.: US 11,795,431 B2
(45) Date of Patent: Oct. 24, 2023

(54) ULTRATHIN INTERFACIAL LAYER ON A HYDROGEL TO DIRECT ITS SURFACE PROPERTIES AND CELL ADHESION

(71) Applicant: The Trustees of Princeton University, Princeton, NJ (US)

(72) Inventors: Jeffrey Schwartz, Princeton, NJ (US); Jeffrey Chen, Redmond, WA (US); Kelly Lim, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 710 days.

(21) Appl. No.: 16/639,427

(22) PCT Filed: Aug. 17, 2018

(86) PCT No.: PCT/US2018/046879
§ 371 (c)(1),
(2) Date: Feb. 14, 2020

(87) PCT Pub. No.: WO2019/036594
PCT Pub. Date: Feb. 21, 2019

(65) Prior Publication Data
US 2021/0130771 A1 May 6, 2021

Related U.S. Application Data

(60) Provisional application No. 62/546,885, filed on Aug. 17, 2017.

(51) Int. Cl.
| | |
|---|---|
| *C12N 5/00* | (2006.01) |
| *A61L 27/38* | (2006.01) |
| *A61L 27/52* | (2006.01) |
| *A61L 27/54* | (2006.01) |
| *C12N 5/071* | (2010.01) |
| *C12N 5/0786* | (2010.01) |
| *C12N 5/077* | (2010.01) |

(52) U.S. Cl.
CPC .......... *C12N 5/0068* (2013.01); *A61L 27/383* (2013.01); *A61L 27/52* (2013.01); *A61L 27/54* (2013.01); *C12N 5/066* (2013.01); *C12N 5/067* (2013.01); *C12N 5/069* (2013.01); *C12N 5/0629* (2013.01); *C12N 5/0645* (2013.01); *C12N 5/0654* (2013.01); *C12N 5/0655* (2013.01); *C12N 5/0656* (2013.01); *C12N 5/0657* (2013.01); *C12N 5/0658* (2013.01); *C12N 5/0661* (2013.01); *A61L 2430/32* (2013.01); *C12N 2500/20* (2013.01); *C12N 2533/30* (2013.01); *C12N 2533/74* (2013.01); *C12N 2533/78* (2013.01); *C12N 2533/90* (2013.01); *C12N 2537/10* (2013.01); *C12N 2539/00* (2013.01)

(58) Field of Classification Search
None
See application file for complete search history.

(56) References Cited

U.S. PATENT DOCUMENTS

| | | |
|---|---|---|
| 5,112,676 A | 5/1992 | Cot et al. |
| 5,827,641 A | 10/1998 | Parenteau et al. |
| 6,020,148 A | 2/2000 | Osborne et al. |
| 9,176,116 B2 | 11/2015 | Schmolz |
| 2004/0001959 A1 | 1/2004 | Schwartz et al. |
| 2004/0258726 A1 | 12/2004 | Stupp et al. |
| 2007/0196663 A1 | 8/2007 | Schwartz et al. |
| 2016/0097938 A1 | 4/2016 | Qiu et al. |
| 2017/0101628 A1 | 4/2017 | Ingber et al. |

FOREIGN PATENT DOCUMENTS

| | | |
|---|---|---|
| WO | 2016118349 A1 | 7/2016 |
| WO | 2019036594 A1 | 2/2019 |

*Primary Examiner* — Allison M Fox
(74) *Attorney, Agent, or Firm* — FOX ROTHSCHILD LLP (57) ABSTRACT

A method is disclosed for coating and patterning hydrogels in order to modify surface properties. The method exploits the water content of the hydrogel and the hydrophobicity of the reaction solvent to create a thin oxide adhesion layer on the hydrogel surface. This oxide adhesion layer enables rapid transformation of the hydrophilic, cell non-adhesive hydrogel into either a highly hydrophobic or a cell-adhesive hydrogel by reaction with an alkylphosphonic acid or an α,ω-diphosphonoalkane, respectively. Also disclosed are coated, patterned hydrogels and constructs comprising the coated, patterned hydrogels.

17 Claims, 3 Drawing Sheets

ULTRATHIN INTERFACIAL LAYER ON A HYDROGEL TO DIRECT ITS SURFACE PROPERTIES AND CELL ADHESION

CROSS-REFERENCE TO RELATED APPLICATION

This application claims the benefit of priority of U.S. Provisional Application No. 62/546,885 filed on Aug. 17, 2017, the disclosure of which is incorporated herein by reference in its entirety.

FIELD OF THE INVENTION

The present invention is related to the field of hydrogels, and specifically to hydrogels having modified surface properties. The inventive hydrogels are coated with an ultrathin surface layer that is capable of directing the surface properties. Such coated hydrogels have utility as scaffolds for reconstructive medicine, including uses in neural regeneration.

BACKGROUND

Hydrogels are an ubiquitous class of materials having utilities ranging from fundamental studies of cell behavior to current and future applications in biomedical devices. Their potential for implementation as scaffolds to address neural injuries is of particular interest. In many cases the hydrogel is based on a synthetic (e.g., polyethylene glycol or polyacrylate) or a natural (e.g., alginate) hydrophilic polymer. The surface properties of these hydrogel materials need to be adjusted according to the desired utility, to affect their hydrophilicity and/or to control cell adhesion and spreading on the hydrogels. Various methods have been developed to these ends, in which surface modification of a hydrogel that is non-adhesive toward cells may entail, for example, introduction of exogenous, cell-adhesive function groups, large molecule surface adsorption on preformed hydrogels, or incorporation of cell adhesive monomers during polymerization to form the hydrogel polymer. Some of these methods require specialized equipment and materials. Such routes are suboptimal with regard to the ease, flexibility and scalability of their implementation, and are also suboptimal with respect to reaction conditions that must be employed for derivatization.

SUMMARY

It has now been discovered that a two-step method can be effected rapidly on a hydrated hydrogel, which provides a bonded coating that enables control of the hydrogel's surface properties. The present method requires no specialized techniques or materials. Instead, it exploits the water content of the hydrogel itself, in a process that uses surface water on the hydrogel and the hydrophobicity of the reaction solvent to create a thin inorganic oxide coating on the hydrogel surface. This inorganic oxide (e.g., $TiO_2$ or $ZrO_2$) then serves as an adhesion layer to control the hydrophilicity/hydrophobicity or cell adhesive properties of the hydrogel through implementing a second synthesis step to grow self-assembled monolayers (SAMs) on the coated hydrogel substrate. The SAM can be a self-assembled monolayer of a cell-adhesive phosphonate (SAMP), preferably an α,ω-diphosphonate. The ease and versatility of this method stands in sharp contrast to known methods for hydrogel surface function modification.

One aspect of the invention is directed to a coated hydrogel comprising an inorganic oxide adhesion layer bonded to the surface of an at least partially hydrated, biocompatible, cross-linked hydrophilic polymer hydrogel, where the inorganic oxide is selected from the group consisting of the oxides of Ti, Zr, Al, Mg, Si, Zn, Mo, Nb, Ta, Sn, W, and V. Preferably the inorganic oxide of the coated hydrogel is selected from the group consisting of the oxides of Al, Ti, Zr, Si, Mg and Zn. The oxide adhesion layer can comprise a pattern over at least part of the hydrogel surface. The pattern can comprise continuous stripes spanning at least part of the hydrogel surface, comprising a tissue growth region.

The hydrated, biocompatible, hydrophilic polymer hydrogel contains at least 10 nmol of water/cm$^2$ at the surface or available to the surface of the hydrogel. The biocompatible hydrophilic polymer hydrogel can also be fully hydrated.

The biocompatible, hydrophilic polymer is a cross-linkable polymer and can be selected from the group consisting of polyethylene glycol, polyacrylate, and polyvinyl alcohol. The cross-linkable polymer can be a cross-linkable polysaccharide or polysaccharide derivative selected from the group consisting of polysaccharides, alginates, hyaluronic acids, guar gum, xanthan gum, carrageenan, methyl cellulose, carboxymethyl cellulose, ethyl methyl cellulose, hydroxypropyl cellulose, and hypromellose. The cross-linkable polymers can be cross-linked with fumarate. Preferably the biocompatible hydrophilic polymer is oligo(polyethylene glycol) fumarate (OPF).

The coated hydrogel can further comprise a self-assembled monolayer (SAM) bonded to the adhesion layer, where the SAM is selected from organic compounds comprising a phosphonic, carboxylic, sulfonic, phosphinic, phosphoric, sulfinic, or hydroxamic group. Preferably the SAM comprises a self-assembled monolayer of phosphonates (SAMP). The phosphonates can be selected from the group consisting of hydrophobic phosphonates and cell-adhesive phosphonates.

The hydrophobic and cell-adhesive phosphonates can be selected from the group consisting of phosphonic acids of structure where the R group is selected from the group consisting of optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted arylalkyl, optionally substituted heteroaryl, and optionally substituted heteroarylalkyl, where heteroalkyl, heteroalkenyl, heteroalkynyl, heteroaryl and heteroarylalkyl contain one or more heteroatoms selected from the group consisting of O, N and S. Preferably the hydrophobic phosphonates are selected from the group consisting of R=$C_3$-$C_{30}$ alkyl. Preferably the cell-adhesive phosphonates are selected from the group consisting of R=$C_3$-$C_{30}$ alkyl substituted with a cell-adhesive group, such as an additional phosphonate group. More preferably the cell-adhesive phosphonates are selected from the group consisting of $C_3$-$C_{30}$ α,ω-diphosphonates.

Another aspect of the invention is directed to a construct for regenerative medicine comprising the coated hydrogel containing a SAM or SAMP bonded to the inorganic oxide coating. The construct can further comprise cells attached to the SAM- or SAMP-coated surface of the hydrogel. The cells are preferably selected from the group consisting of fibroblasts, endothelial cells, keratinocytes, osteoblasts, chondroblasts, chondrocytes, hepatocytes, macrophages, cardiac muscle cells, smooth muscle cells, skeletal muscle cells, tendon cells, ligament cells, epithelial cells, stem cells, neural cells, PC12 cells, neural support cells, Schwann cells, radial glial cells, cells that form neurospheres, neural tumor cells, glioblastoma cells and neuroblastoma cells. The fibroblasts preferably comprise NIH 3T3 fibroblasts. The construct can further comprise an extracellular matrix (ECM). The construct can be further decelluarized, leaving the ECM attached.

Yet another aspect of the invention is directed to a method of coating a hydrogel with an inorganic oxide adhesion layer, comprising the steps of: a) providing a hydrogel which is at least partially hydrated, and optionally containing a pattern mask pressed into the hydrogel surface; b) providing a coating mixture comprising an anhydrous hydrophobic solvent containing a water-reactive inorganic compound that is dissolved and/or dispersed in the solvent; and c) suspending the hydrogel in the coating solution for a time and temperature sufficient to form an inorganic oxide coating at the solvent interface on the surface of the hydrogel thereby providing a coated hydrogel, where the inorganic compound is selected from the group consisting of the alkoxides, alkyls, amides and halides of Ti, Zr, Al, Mg, Si, Zn, Mo, Nb, Ta, Sn, W, and V. The method can further comprise: d) removing the coated hydrogel from the coating solution; and e) rinsing with a solvent to provide a rinsed coated hydrogel. The method can still further comprise: f) heating the rinsed coated hydrogel to 30 to 40° C., and removing the optional pattern mask.

The inorganic compound of the method can be selected from the group consisting of the alkoxides of Al, Ti, Zr, Si, Mg and Zn. The alkoxide can be selected from the group consisting of methoxide, ethoxide, propoxide, iso-propoxide, butoxide, iso-butoxide, sec-butoxide, and tert-butoxide. The inorganic compound of the method can be an inorganic alkyl, an inorganic amide or an inorganic halide. Preferably the inorganic halide is the chloride.

BRIEF DESCRIPTION OF THE DRAWINGS

FIGS. 2A, 2B, 2C, 2D and 2E show optical images of NIH 3T3 cells plated on SAMPs at 150,000 cells/well. All images are 20×: After 5 days (FIG. 2A) phase contrast image of cells plated on $C_{12}$-derived SAMP; (FIG. 2B) stained for F-actin; (FIG. 2C) stained for fibronectin; (FIG. 2D) matrix stained for fibronectin after decellularization; (FIG. 2E) matrix stained for fibronectin after 26 days following decellularization.

DETAILED DESCRIPTION

As used herein the term "ultrathin" refers to a layer of inorganic oxide that is about 0.3 nm to about 20 nm thick, which corresponds to 1 to about 20 monolayers of oxide, vide infra. The term "hydrogel" refers to a hydrophilic polymer, preferably cross-linked, which readily loads with water. A hydrogel typically is highly oxygenated with functional groups such as hydroxyl, ethers and carboxylic acids or carboxylate salts. The hydrogels useful in the present invention are preferably compatible with biomedical applications and can be synthetic, such as PEG derivatives, polyacrylamides and silicones, or natural polymers, such as polysaccharides, alginates, hyaluronic acids, gums (guar, xanthan, carrageenan), methyl cellulose, carboxymethyl cellulose, ethyl methyl cellulose, hydroxypropyl cellulose, and hypromellose. The term "full hydration" refers to a hydrogel fully saturated with water, i.e., to its maximum holding capacity. The term "partial hydration" refers to a hydrogel that contains at least sufficient water on its surface, or available to the surface, to react with a water-reactive inorganic compound forming the desired inorganic oxide coating. At least 10 nmol of water/$cm^2$ should be at the surface or available to the surface of the hydrogel polymer, vide infra. As used herein, the term "hydrophobic solvent" means a solvent that sequesters water. Suitable hydrophobic solvents include hydrocarbons, and halogenated hydrocarbons such as chlorinated and fluorinated hydrocarbons. The hydrocarbons can include aromatic solvents such as xylenes and toluene, and alkanes such as $C_4$-$C_{22}$ straight, branched or cyclic alkanes. Preferably the aromatic solvents are xylenes and toluene. Preferably the alkane hydrocarbon solvents are $C_5$ to $C_{20}$ hydrocarbons, straight, branched or cyclic. These can include pentane, hexane, heptane, octane, and their isomers. The cyclic hydrocarbons can include cyclopentane, cyclohexane, cycloheptane, cyclooctane, etc. The hydrophobic solvent should not be strongly bound to the hydrogel, which would preclude the intended biocompatible use of the coated hydrogel. As used herein the term "bonded" means affixed or attached, preferably coordinatively or covalently attached. Unless otherwise noted, as used herein the term "about" refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4.

The surface of the hydrogel can be patterned or unpatterned. The patterned hydrogel surface can be in various configurations. Preferably, for tissue growth and alignment, continuous oxide layer stripes are deposited across the hydrogel surface of the tissue growth region, and each continuous oxide stripe layer spans the entire length of the tissue growth surface. A stripe is typically continuous for at least about 2 mm up to the entire length of the hydrogel base layer. The stripes can be 2-20 mm or longer, depending on the size of the hydrogel base layer and the construct to be fabricated: at least 2 mm, or 5 mm, or 10 mm, or 15 mm, or 20 mm or longer. The tissue growth surface preferably has an alternating pattern of continuous oxide stripes with hydrogel surface stripes therebetween. Preferably the oxide layer stripes are about 10 µm to about 100 µm wide separated by hydrogel base layer stripes about 10 µm to about 100 µm wide. More preferably, stripe patterned arrays have oxide layer stripes about 10 µm to about 30 µm wide separated by base layer stripes about 10 µm to about 30 µm wide. Examples include, without limitation, oxide stripes about 10 µm wide and base layer stripes about 30 µm wide, or about 20 µm wide and about 30 µm wide, or about 30 µm wide and about 30 µm wide, or about 20 µm wide and about 20 µm wide, or about 20 µm wide and about 10 µm wide, or about 10 µm wide and about 10 µm wide, respectively.

Alignment was quantified on each surface using Fast Fourier Transform (FFT) analysis by measuring the aspect ratio of the FFT output image. The aspect ratio was derived by dividing the vertical dimension of the oval output pattern by the horizontal dimension of the oval pattern that is produced by the FFT. The FFT output produces an image in which the width of the oval (the horizontal dimension) is rotated 90° with regard to the (vertical) pattern direction; thus perfect alignment with a pattern that is vertical on the page would generate an FFT that is a perfect horizontal line. Therefore, the longer the horizontal dimension and the shorter the vertical dimension of the oval pattern (giving the smallest numerical ratio), the better the alignment of the cells with the pattern; perfect alignment would have a ratio of close zero. Thus, smaller numerical values of the ratio indicate better alignment. In practice, values such as about 0.2 to about 0.6 are obtained, indicating good alignment. Typical values are 0.5 to 0.6. Values of 0.9 to 1.0 indicate an unaligned matrix.

The patterning of hydrogels requires different techniques from those discovered previously by the present inventors, or those known in the prior art. In order to apply the oxide coating in a patterned way to the soft surface of a hydrated hydrogel, the hydrogel was debossed with a shadow mask so that the oxide could be placed on raised ridges of hydrogel. Shadow masks were prepared by laser-cutting stripes in sheets of KAPTON® polyimide film; masks consisting of ablated stripes about 10 µm to about 100 µm wide that were separated by unablated KAPTON® stripes about 10 µm to about 100 µm wide were typically used. The KAPTON® film was preferably 20 µm to 50 µm thick. Striped KAPTON® masks of about 30 µm×30 µm were typically prepared and used.

Dried OPF was typically cut into 5 mm×5 mm squares and hydrated with water to form 1 cm×1 cm hydrated OPF squares, the swelling of the polymer being due to the uptake of water. The samples were then rinsed with deionized water and gently dried. The laser-ablated KAPTON® shadow mask was placed onto the OPF such that the striped area was directly in contact with the OPF surface. The OPF-mask composite was heated to 30° C., and the mask was depressed into the OPF (debossing) using an appropriate weight, thereby creating raised stripes of hydrogel which emerge through the ablated regions of the mask. Heating with the mask in place was continued briefly, and excess water was removed from the surface of the OPF-mask ensemble. The ensemble was then immersed in a metal oxide precursor solution for an appropriate period of time. The ensemble was removed, rinsed and then was heated to 30° C. briefly. This process created a layer of cross-linked oxide that was patterned on the raised OPF surface since only the regions of the OPF that are not covered by the KAPTON® shadow mask (the ablated stripes) are exposed to the solution of the titanium or zirconium alkoxide. The ensemble was removed from heat and allowed to cool before being immersed in a phosphonic acid solution to form a SAMP, again in raised stripes emerging through the ablated regions of the mask. Cell adhesive stripes on the oxide covered areas of the raised OPF surface were formed using, for example, 1,12-dodecanediphosphonic acid; hydrophobic stripes were formed using, for example, octadecylphosphonic acid. The KAPTON® mask was then separated mechanically from the OPF surface and the patterned OPF was heated at 30° C. briefly. Thus, raised SAMP stripes are created in the hydrogel by the masking process aspect of the invention. Freshly prepared patterned OPF samples were stored either under water or PBS.

One aspect of the invention is directed to a coated hydrogel comprising an inorganic oxide adhesion layer bonded to the surface of an at least partially hydrated, biocompatible, cross-linked hydrophilic polymer hydrogel, where the inorganic oxide is selected from the group consisting of the oxides of Ti, Zr, Al, Mg, Si, Zn, Mo, Nb, Ta, Sn, W, and V. Preferably the inorganic oxide of the coated hydrogel is selected from the group consisting of the oxides of Al, Ti, Zr, Si, Mg and Zn.

With regard to the inorganic oxide coating, the non-oxygen inorganic species is preferably not toxic in reconstructive medicine applications, and can be advantageously selected from the group consisting of Ti, Zr, Al, Mg, Si, Zn, Mo, Nb, Ta, Sn, W, and V. Preferably the inorganic species is Al, Ti, Zr, Si, Mg or Zn. More preferably the inorganic species is Al, Si, Ti or Zr. The inorganic species can be Al. The inorganic species can be Ti. The inorganic species can be Zr. The inorganic species can be Mg. The inorganic species can be Si. The inorganic species can be Zn. The inorganic species can be Mo. The inorganic species can be Nb. The inorganic species can be Ta. The inorganic species can be Sn. The inorganic species can be W. The inorganic species can be V.

The thicknesses of inorganic oxide layers applied by various methods has been measured for comparison with the present method. Vapor deposition on various non-hydrogel polymeric surfaces (using, for example $Zr(O-tBu)_4$) ranges from about 1-10 nanometers. Since each oxide "monolayer" is about 0.3 nm thick, this translates to about 3-30 monolayers. For hydrogels, using the presently disclosed method, and without wishing to be bound by any particular theory, the number of monolayers formed depends on the ability of water to transport through the first-applied oxide monolayer, so that further layers can be formed by the above-described reaction with water. As water movement through the first applied oxide monolayer does not appear to be limiting, an ultrathin layer of about 0.3 nm (1 monolayer) to about 20 nm (60 monolayers) thickness is observed. The ultrathin oxide layer is preferably about 0.3 to about 15 nm, or about 0.3 to about 10 nm, or about 0.3 to about 5 nm, or about 0.3 to about 1 nm thick. The ultrathin layer of oxide can be about 0.3 nm, or about 0.5 nm, or about 1 nm, or about 2 nm, or about 3 nm, or about 4 nm, or about 5 nm, or about 10 nm, or about 15 nm, or about 20 nm thick.

Surprisingly it has been discovered that the hydrated, biocompatible, hydrophilic polymer hydrogel can contain as little as 10 nmol of water/cm$^2$ at the surface or available to the surface of the hydrogel, in order for the ultrathin inorganic oxide coating to form. The available surface water can be at least 10, or at least 12, or at least 14, or at least 16, or at least 18, or at least 20 nmol/cm². The biocompatible hydrophilic polymer hydrogel can also be fully hydrated.

The biocompatible hydrophilic polymer is a cross-linkable polymer and can be selected from the group consisting of polyethylene glycol, polyacrylate, and polyvinyl alcohol. The cross-linkable polymer can be a cross-linkable polysaccharide or polysaccharide derivative selected from the group consisting of polysaccharides, alginates, hyaluronic acids, guar gum, xanthan gum, carrageenan, methyl cellulose, carboxymethyl cellulose, ethyl methyl cellulose, hydroxypropyl cellulose, and hypromellose (hydroxypropyl methyl cellulose). The cross-linkable polymers can be cross-linked with fumarate or other linking agents. Preferably the biocompatible hydrophilic polymer is oligo(polyethylene glycol) fumarate (OPF).

The coated hydrogel can further comprise a self-assembled monolayer (SAM) bonded to the adhesion layer, where the SAM is selected from organic compounds comprising a phosphonic, carboxylic, sulfonic, phosphinic, phosphoric, sulfinic, or hydroxamic group. Preferably the SAM comprises a self-assembled monolayer of phosphonates (SAMP). The phosphonates can be selected from the group consisting of hydrophobic phosphonates and cell-adhesive phosphonates. These hydrophobic and cell-adhesive phosphonates can be selected from the group consisting of phosphonic acids having the structure:

where the R group is selected from the group consisting of optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted arylalkyl, optionally substituted heteroaryl, and optionally substituted heteroarylalkyl, where heteroalkyl, heteroalkenyl, heteroalkynyl, heteroaryl and heteroarylalkyl contain one or more heteroatoms selected from the group consisting of O, N and S. The optional substitution on the R group can comprise one or more groups selected from halogen, alkoxy, hydroxyl, amino, carboxylic acid, carboxylate ester, phosphonic acid, phosphonate, ether, alkyne, azide, thiol, polyol moieties and sugar alcohol moieties.

Preferably the hydrophobic phosphonates are selected from the group consisting of R=$C_3$-$C_{30}$ alkyl, optionally substituted with halogen or alkoxy. The alkyl group can be a $C_5$-$C_{24}$ alkyl, or a $C_6$-$C_{20}$ alkyl, or a $C_8$ to $C_{18}$ alkyl. The alkyl group can be a $C_3$, $C_4$, $C_6$, $C_8$, $C_{10}$, $C_{12}$, $C_{14}$, $C_{16}$, $C_{18}$, or $C_{20}$ alkyl group, all of which can be optionally substituted with halogen or alkoxy.

Preferably the cell-adhesive phosphonates are selected from the group consisting of R=$C_3$-$C_{30}$ alkyl substituted with a further phosphonate group. The alkyl group can be a $C_4$-$C_{24}$ alkyl, or a $C_6$-$C_{20}$ alkyl, or a $C_8$ to $C_{18}$ alkyl. The alkyl group can be a $C_3$, $C_4$, $C_6$, $C_8$, $C_{10}$, $C_{12}$, $C_{14}$, $C_{16}$, $C_{18}$, or $C_{20}$ alkyl group. More preferably the cell-adhesive phosphonates are selected from the group consisting of $C_3$-$C_{30}$ α,ω-diphosphonates. In this case the alkylene group between the phosphonate moieties can be a $C_3$, $C_4$, $C_6$, $C_8$, $C_{10}$, $C_{12}$, $C_{14}$, $C_{16}$, $C_{18}$, $C_{20}$, $C_{22}$, $C_{24}$, $C_{26}$, $C_{28}$, or $C_{30}$ alkylene group. The α,ω-diphosphonic acid can be a $C_{3-16}$ α,ω-diphosphonic acid, preferably a $C_{4-12}$ α,ω-diphosphonic acid, more preferably a $C_4$, or a $C_6$, or a $C_8$, or a $C_{10}$, or a $C_{12}$ α,ω-diphosphonic acid. The α,ω-diphosphonic acid can be 1,4-butanediphosphonic acid, or 1,6-hexanediphosphonic acid, or 1,8-octanediphosphonic acid, or 1,10-decanediphosphonic acid, or 1,12-dodecanediphosphonic acid, or mixtures of two or more thereof.

Preferably the SAMP of the coated construct comprises a phosphonic acid covalently attached to the inorganic oxide adhesion layer, which phosphonic acid contains functionality adapted for cell binding. As noted above, the cell-binding phosphonic acid can comprise one or more functional groups selected from polyol moieties, sugar alcohol moieties, alkoxy, hydroxyl, amino, carboxylic acid, carboxylate ester, phosphonic acid, phosphonate, ether, alkyne, azide and thiol. Preferably the phosphonic acid is a diphosphonic acid, more preferably an α,ω-diphosphonic acid as described above.

Another aspect of the invention is directed to a construct for regenerative medicine comprising the coated hydrogel containing a SAM or SAMP bonded to the raised inorganic oxide coating. The construct can further comprise cells attached to the SAM- or SAMP-coated surface of the hydrogel. The cells are preferably selected from the group consisting of fibroblasts, endothelial cells, keratinocytes, osteoblasts, chondroblasts, chondrocytes, hepatocytes, macrophages, cardiac muscle cells, smooth muscle cells, skeletal muscle cells, tendon cells, ligament cells, epithelial cells, stem cells, neural cells, PC12 cells, neural support cells, Schwann cells, radial glial cells, cells that form neurospheres, neural tumor cells, glioblastoma cells and neuroblastoma cells. The fibroblasts preferably comprise NIH 3T3 fibroblasts. The construct can further comprise an extracellular matrix (ECM). The ECM is a collection of extracellular molecules secreted and assembled by cells that provides structural and biochemical support to the surrounding cells. The construct can be further decelluarized, leaving the ECM attached.

Yet another aspect of the invention is directed to a method of coating a hydrogel with an inorganic oxide adhesion layer, comprising the steps of: a) providing a hydrogel which is at least partially hydrated as defined above, and optionally containing a pattern mask pressed into the hydrogel surface; b) providing a coating mixture comprising an anhydrous hydrophobic solvent containing a water-reactive inorganic compound which is dissolved and/or dispersed in the solvent; and c) suspending the hydrogel in the coating solution for a time and temperature sufficient to form an inorganic oxide coating at the solvent interface on the surface of the hydrogel to provide a coated hydrogel; where the inorganic compound is selected from the group consisting of the alkoxides, alkyls, amides and halides of Ti, Zr, Al, Mg, Si, Zn, Mo, Nb, Ta, Sn, W, and V. The method can further comprise: d) removing the coated hydrogel from the coating solution; and e) rinsing with a solvent to provide a rinsed coated hydrogel. The method can still further comprise: f) heating the rinsed coated hydrogel to a temperature which does not compromise the integrity of the 3-dimensional structure of the hydrogel, preferably about 30 to about 40° C., and removing the optional pattern mask.

The inorganic compound of the method can be selected from the group consisting of the alkoxides of Al, Ti, Zr, Si, Mg and Zn. The alkoxide can be selected from the group consisting of methoxide, ethoxide, propoxide, iso-propoxide, butoxide, iso-butoxide, sec-butoxide, and tert-butoxide. The inorganic compound of the method can be an inorganic alkyl, an inorganic amide or an inorganic halide. Preferably the inorganic halide is the chloride.

With regard to the inorganic water-reactive compound, the inorganic species can be advantageously selected from the group consisting of Ti, Zr, Al, Mg, Si, Zn, Mo, Nb, Ta, Sn, W, and V. Preferably the inorganic species is Al, Ti, Zr, Si, Mg or Zn. More preferably the inorganic species is Al, Si, Ti or Zr. The inorganic species can be Al. The inorganic species can be Ti. The inorganic species can be Zr. The inorganic species can be Mg. The inorganic species can be Si. The inorganic species can be Zn. The inorganic species can be Mo. The inorganic species can be Nb. The inorganic species can be Ta. The inorganic species can be Sn. The inorganic species can be W. The inorganic species can be V. With regard to the ligands of the inorganic water-reactive compound, these can be selected from the group consisting of alkoxides, amides, halides and alkyls. The ligands can be alkyls. A preferred alkyl is methyl or ethyl. The ligands can be halides. A preferred halide is chloride. The ligands can be alkoxides. Preferred alkoxides are selected from the group consisting of methoxide, ethoxide, propoxide, iso-propoxide, butoxide, iso-butoxide, sec-butoxide, and tert-butoxide.

Figure 1:
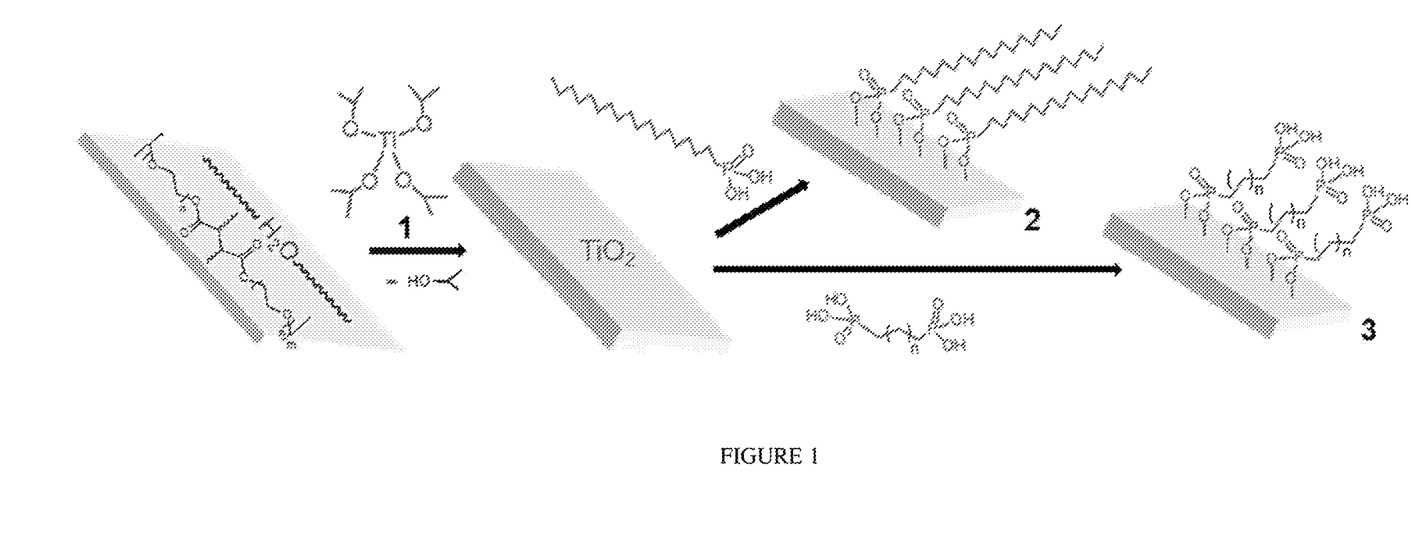
FIG. 1 shows the scheme for SAMP formation on fully hydrated, hydrophilic, cell non-adhesive oligo(polyethylene glycol) fumarate (OPF) hydrogel. The substrate is placed in a solution of tetra(iso-propyl)titanium (1), and surface water reacts to give a thin $TiO_2$ surface layer, which subsequently reacts with a hydrophobic phosphonic acid, such as octadecylphosphonic acid (ODPA), to yield hydrophobic hydrogel 2, or with a cell adhesive phosphonic acid, such as an α,ω-(diphosphono)alkane, to yield cell adhesive hydrogel 3.
Figure 2A:
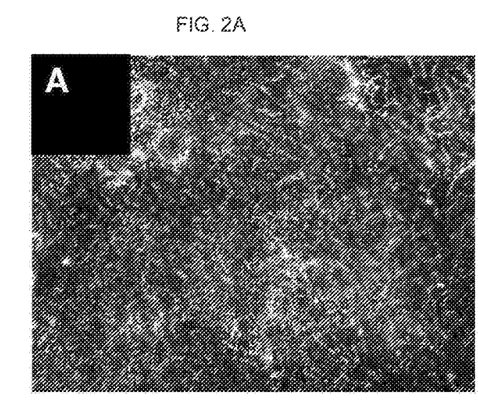
Figure 2B:
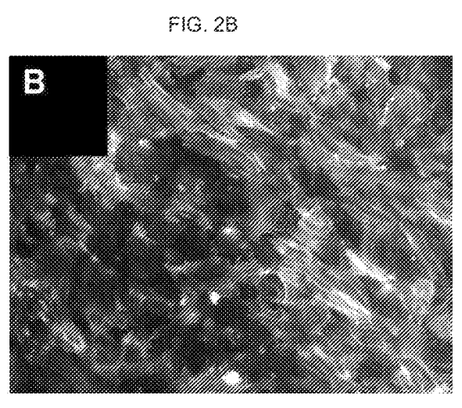
Figure 2C:
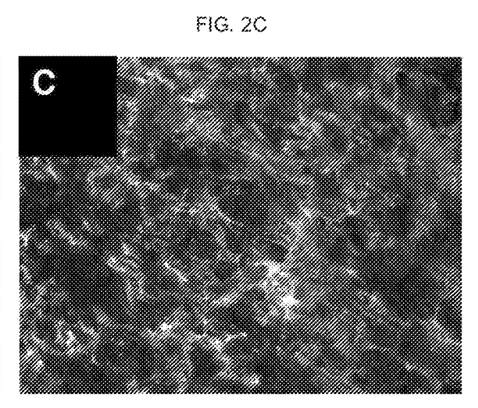
Figure 2D:
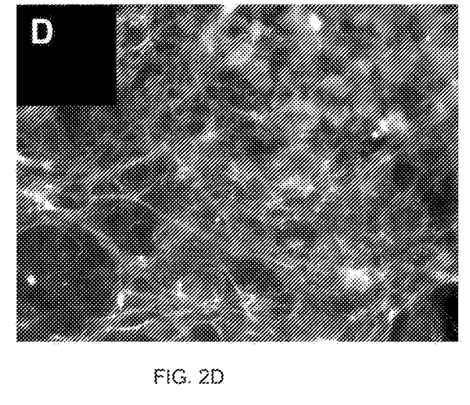
Figure 2E:
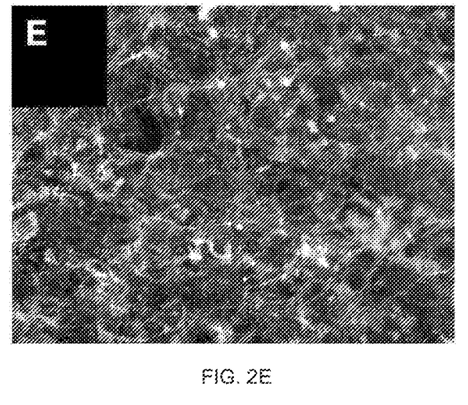
Figure 3A:
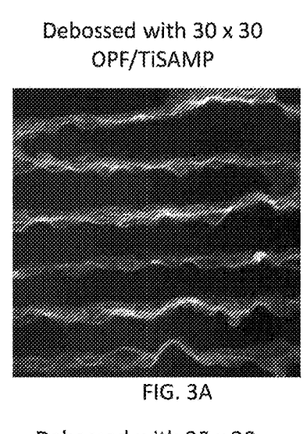
FIGS. 3A, 3B, 3C, 3D, 3E, 3F, 3G and 3H show optical images of NIH 3T3 cells plated on linearly patterned versus unpatterned (i.e., fully debossed with the SAMP) OPF/Ti SAMP and OPF/Zr SAMP. After 1 day of culturing, the patterned SAMPs clearly show cell alignment with the pattern SAMP stripes (FIGS. 3A and 3C), whereas their respective fully SAMP-coated counterparts show cell coverage without spatial organization (FIGS. 3B and 3D). This is reflected in the Fast Fourier Transform (FFT) analysis (Table 4). By day 5, cells have bridged the cell-non-adhesive space to form a confluent layer (FIGS. 3E and 3G), which shows alignment with the original SAMP pattern (see the FFT data in Table 4). By day 5 the fully SAMP-coated counterparts show denser cell coverage, but no spatial organization (FIGS. 3F and 3H) as reflected in the FFT analysis (Table 4).
Figure 3B:
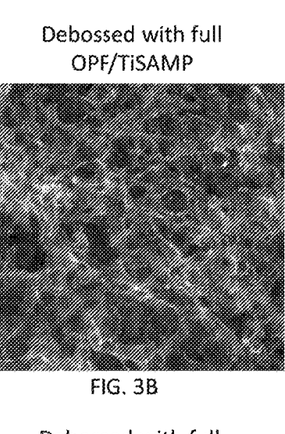
Figure 3C:
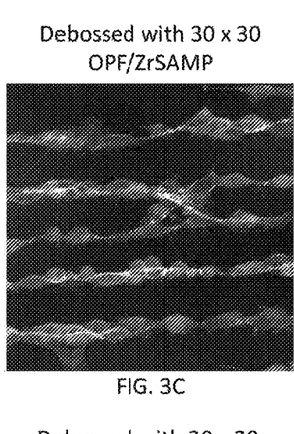
Figure 3D:
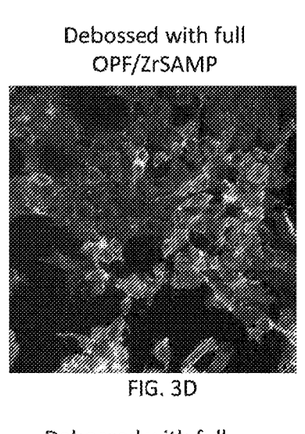
Figure 3E:
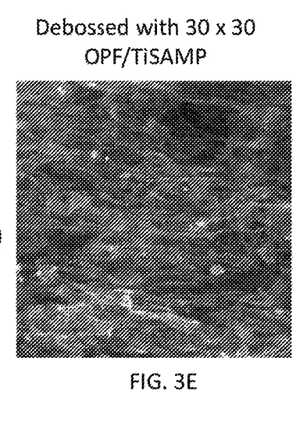
Figure 3F:
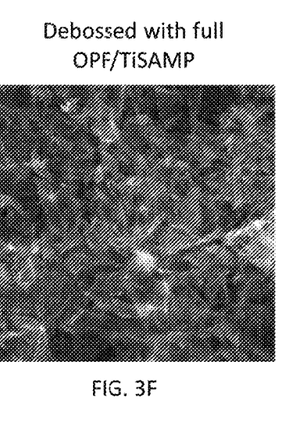
Figure 3G:
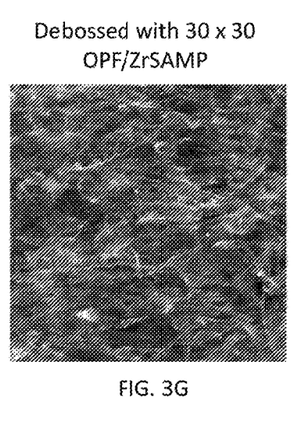
Figure 3H:
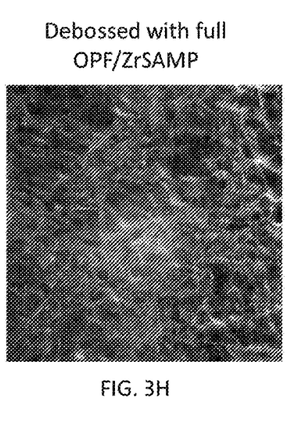

One aspect of the invention can be implemented as follows. Friable sheets of superficially dried, 0.08 mm thick oligo(polyethylene glycol) fumarate (OPF) were provided by the Mayo Clinic, Rochester, Minn.; they swell and become mechanically fragile on rehydration in MilliQ® water (under these conditions, a 4 mm×4 mm coupon of "dry" OPF swells to about 12 mm×12 mm). In a typical experiment, a rehydrated coupon was razor cut to 1 cm×1 cm and then put in a solution of 30 µL of a titanium alkoxide, such as titanium iso-propoxide (1), in 5 mL of a hydrophobic solvent, such as xylene (toluene or hexane are comparable for use) for about 1 min. A rapid reaction occurred at the coupon surface, presumably by hydrolysis with hydrogel-supplied water, and cross-linking of hydroxytitanium species thus formed produced a thin surface coating of white titanium dioxide, identified by electron-dispersive X-ray spectroscopy (EDS) analysis. If a hydrophilic solvent such as iso-propanol was used instead, rapid hydrolysis occurred in the supernatant as well as at the coupon surface and the coupon physically distorted; both effects are apparently due to solvent-assisted dehydration of the hydrogel, and the precipitated $TiO_2$ coating was not firmly attached and easily spalled from the surface. The coupon coated using a hydrophobic solvent, was removed from solution, gently rinsed with iso-propanol, and heated on a glass plate to 35° C. for about 1 min to further cross-link surface Ti species. No ostensible physical changes were observed for heating at this temperature; however, noticeable curling of samples was noted when the heating temperature was >40° C. On cooling to room temperature, the coupon was immersed in a solution of a phosphonic acid for about 1 hr, then rinsed and warmed to 35° C. for 1 min to ensure formation of the phosphonate monolayer (SAMP); see FIG. 1.

Octadecylphosponate (ODPA) was chosen as a diagnostic ligand of SAMP formation (2.5 mg ODPA in 5 mL of toluene or xylene); water wetting contact angle measurements and infrared (IR) spectroscopy could then be used to assess the SAMP structure and interface stability. IR spectroscopy of six coupons, at three locations on each, showed $\nu_{CH2antisymm}$ at 2918-2915 $cm^{-1}$, indicating a well-ordered phosphonate monolayer (2 of FIG. 1). As a control, it was determined that ODPA does not adhere to hydrated OPF in the absence of the $TiO_2$ adhesion layer. To determine the stability of the interface-SAMP ensemble, IR spectroscopy was used to examine effects of ethanol rinsing of treated coupons, as well as their immersion in phosphate-buffered saline (PBS) for up to 7 days. Neither procedure resulted in significant loss in IR signal intensity or change in position for this characteristic indicator of film content and order, after any weakly adsorbed multilayer was rinsed away.

The hydrophobicity imparted to the ODPA/$TiO_2$-terminated, fully hydrated hydrogel was shown in at least two ways. First, the coupon floated on the surface of PBS, and second, it resisted contact angle measurement for water wetting because drops of water would not transfer easily from a needle tip to the ODPA-terminated surface. Indeed, if the pipette were placed close to the surface, the test drop of water would literally bounce off the surface back onto the pipette tip (a greater pipette-to-surface separation enabled measurement of the contact angle to be >115°. Further, a water droplet simply rolled off a slightly tilted coupon surface. Although a hydrophobic hydrogel has been reported by coating the surface with a layer of hydrophobic microparticles, the present method is the first to show this dramatic change in hydrogel surface property by self-assembled monolayer formation.

Although OPF is a desirable substrate for neural regeneration scaffolds and devices it is not cell-adhesive. It was therefore of particular interest to demonstrate that the present SAMP/$TiO_2$/hydrogel method could render OPF cell-adhesive through a simpler route than any of those already described. Therefore, coupons of $TiO_2$/hydrogel were immersed in solutions of either (1,4-diphosphono)butane or (1,12-diphosphono)dodecane (2.5 mg diphosphonoalkane in 5 mL of toluene or xylene) under the same conditions used to prepare monolayers of ODPA. NIH 3T3 cells were then plated on these SAMP-terminated hydrogels (3 of FIG. 1) at 150,000 cells/well, which were analyzed by microscopy. After 5 days the cells were found to have attached and spread to confluence on the (1,12-diphosphono)dodecane-derived SAMP; cell coverage was less comprehensive on the (1,4-diphosphono)butane-derived SAMP. Shorter chain alkylphosphonate SAMPs are less well ordered than those formed from longer alkyl chain phosphonic acids, and it was observed by IR that diphosphonoalkane SAMPs prepared on various surfaces do not show the organized chain arrangement characteristic of their similar carbon number alkylphosphonate SAMPs. Without wishing to be bound by any particular theory, this is attributed to the spatial demands of the phosphonic acid "tail" group of the α,ω-diphosphonates. It is believed that the differences in observed cell coverage are due to better SAMP formation on the $TiO_2$ adhesion layer by the $C_{12}$-diphosphonic acid than by the $C_4$-diphosphonic acid. Cell confluence was reached 5 days after plating, and decellularization using a mild cell-lysis protocol yielded a cell-assembled extracellular matrix (ECM) that was stable in PBS for at least 26 days.

Thus, it has been demonstrated that a two-step method can be used to prepare a thin adhesion layer on a hydrated hydrogel. It has also been shown that monolayers of organo-phosphonates can be assembled on this adhesion layer. Through choice of the phosphonic acid, a hydrophobic or, especially, a cell-adhesive SAMP termination can be imparted to the otherwise hydrophilic, cell non-adhesive substrate. A hydrophobic SAMP/$TiO_2$/OPF ensemble provided the means to study interface stability. This method utilized the water of the hydrogel, itself, as a reagent to hydrolyze an inorganic water-reactive compound, such as an inorganic alkoxide or an inorganic amide, and to deposit and cross-link a thin coating of an inorganic oxide, such as titanium dioxide, on the hydrogel surface that is delivered to the surface in a hydrophobic solvent. Further, it has been demonstrated that the surface of the hydrogel can be patterned, as disclosed herein. Given its simplicity, and the versatility that is derived from the structural variety of available phosphonic acids, it is believed that the present inorganic oxide/SAMP approach to the control of hydrogel surface properties has the potential not only to augment, but even to replace, many of the complex routes reported for surface treatment of hydrogels.

In summary, the present method converts an otherwise unreactive hydrogel material into one that is reactive at the surface, and this reactive surface can be advantageously patterned. The surface reactivity can be controlled by the top coating layer applied to the surface, so that cell attachment, spreading and ECM formation is possible. Alternatively the hydrogel material, which is inherently hydrophilic, can be made hydrophobic on its surface. Such means to direct the surface properties of hydrogels lead to many possible applications in reconstructive medicine and other biomedical and biological fields.

For example the present patterned hydrogels find potential use in nerve regeneration. Thus, when an OPF/SAMP patterned scaffold as described herein is cultured with fibroblasts, the cells spread and proliferate in register with the raised-patterned surface and an ECM is formed. The organization and alignment of the formed tissue is maintained even over the non-cell-adhesive regions of the pattern, i.e., the native hydrogel valleys. The cell-assembled matrix can be decellularized using published methods. A section of this material can be cut from the coupon, rolled and inserted into the transected spinal cord of a rat. After about 14 weeks nerve regeneration can be assessed by well-known physiological and cytometric methods such as the Basso-Beattie-Breshnahan (BBB) scale.

EXAMPLES

General. Materials. OPF polymer was provided by Dr. Nicolas Madigan (Windebank Lab, Mayo Clinic). OPF samples were hydrated in a glass petri dish using Milli-Q® (MQ) water and then cut into 1 cm×1 cm squares. All hydrated samples were stored in MQ water in scintillation vials, the dehydrated samples were placed in a container and stored inside a desiccator. Milli-Q® ultrapure water was obtained from the Millipore Corporation.

All other materials were procured from commercial sources. Solvents and chemical reagents used in the processing of OPF or other hydrogel polymers include methanol (Sigma Aldrich), iso-propanol (Sigma Aldrich), tert-butanol (Fisher Scientific), 200 proof ethanol (Pharmco-Aaper), xylene (EMD Millipore Corporation), toluene (EMD Chemical Inc.), hexanes (Sigma Aldrich), titanium (IV) iso-propoxide (Sigma Aldrich), 1,4-butanediphosphonic acid (Acros Organics), 1,12-dodecanediphosphonic acid (Sigma Aldrich), and phosphonic acid (Alfa Aesar, Sigma Aldrich).

For general laboratory work, materials included 1 in.×3 in., 1.2 mm thick plain pre-cleaned micro slides (VWR International LL), 20 mL borosilicate scintillation vials (Wheaton), Eppendorf Research® plus single channel 10-100 μL micropipettes, and 9" and 5¾" inches disposable lime glass Pasteur pipets (VWR International LL).

Surface Analysis Techniques. The hydrated hydrogel gradually loses its water content by evaporation and is thus only stable in an aqueous environment. Yet water and other chemicals present under physiological conditions may be factors that degrade the chemical modification. Other methods of analysis are required to accommodate for its hydrated nature. Scanning electron microscopy (SEM) and energy-dispersive X-ray spectroscopy (EDS) are two techniques that have been used to assess the presence and composition of surface modifications. SEM/EDS normally function under high vacuum. Degrading the vacuum by allowing for a gaseous environment temporarily accommodates hydrated samples, but is still damaging to the sample. ATR-FTIR and contact angle goniometry are two ambient techniques that are used to assess monomer film quality and stability.

Contact Angle and Wetting. The hydrophobicity and hydrophilicity of the surface assemblies are most easily evaluated by contact angle measurement, which is related to film surface energy. Contact angle is a surface characterization method used to measure the wetting properties of a material. The technique takes into account the liquid-solid interface and the liquid-vapor interface in providing for angle measurements between the material surface and the base of the droplet. A microliter volume droplet of liquid was placed on the surface. Measurements were acquired by calculating the angle between the tangent line at the intersection of the liquid-vapor interface of the droplet profile and the surface. The conventional telescope-goniomtry method was used. For organic surfaces, water is the most commonly used liquid and is used for wetting measurements in this work. Contact angle measurement were taken using an Attension Theta Optical Tensiometer (KSV Instruments) outfitted with a microliter threaded syringe (Hamilton Co.). The Young-Laplace equation was used to calculate the droplet curvature and tangent angle from the digital images.

Infrared Spectroscopy. Infrared (IR) spectroscopy enables the detection of functional groups in a molecule by identifying unique peaks corresponding to the stretching and bending of chemical bonds. This same technique can be applied to SAMs on both optically transparent (transmission mode) and reflective (grazing angle spectral reflectance mode) substrates. IR can evaluate successful monolayer preparation and monitor degradation, as well as determine the degree of ordering in a SAM surface. Antisymmetric and symmetric methylene stretches are diagnostic peaks for alkyl-based monolayers, and appear in the vicinity of 2920 and 2850 cm$^{-1}$ respectively. The wavenumbers for methylene group stretching modes are understood to be diagnostic of whether the chains exist in an all-trans configuration ("ordered" or crystalline state) or in a random configuration ("disordered" and "liquid-like" film). A well-ordered film in this work is defined to be characterized by antisymmetric methylene stretching wavenumber below 2920 cm$^{-1}$ and symmetric methylene stretching wavenumber below 2850 cm$^{-1}$. To assess film quality, ATR-FTIR data were taken using a Nicolet ™iSTM50 FT-IR Spectrometer.

Energy Dispersive X-Ray Spectroscopy. Energy Dispersive X-Ray Spectroscopy (EDS, EDX, or XEDS) is an analytical technique used for chemical characterization or element analysis of a sample. SEM can be coupled with an EDS detector to identify and quantify elements. The principle underlying EDS is the unique atomic structure of each element. A high-energy beam of charged electrons or other particles is used to stimulate the emission of characteristic X-rays from the specimen. Upon inelastic collision, an inner-shell electron transitions to a higher energy orbital, creating a vacancy. In a short period ($10^{-15}$ s), a higher-energy electron transitions to fill this vacancy and emits a characteristic X-ray unique to each element. An X-ray detector acts as a dispersive device that measures the energies of the emitted X-rays, which are then compiled and plotted as a spectrum.

SEM and EDS characterization was performed at the Imaging and Analysis center of the Andlinger Center for Energy and the Environment at Princeton University, using an FEI Quanta 200 FEG Environmental-SEM equipped with an Oxford INCA Synergy 450 EDS system and an Oxford X-Max 80 mm silicon drift detector. The operating conditions were on either low vacuum (0.53 torr) or environmental mode (7-9 ton). The use of environmental mode required the addition of a Gaseous Secondary Electron Detector (GSED) with a bore of 500 μm. A low electron acceleration voltage (5.00 keV) was used on low vacuum to avoid charging of the substrate, but a higher electron acceleration (20.00-30.00 keV) and greater spot size were used to compensate for the added noise from water vapor under ESEM.

Example 1

Synthesis of TiO$_2$/SAMP Bilayer on OPF

A scintillation vial was filled with Ti(iso-PrO)$_4$ and then solvent (xylene, toluene or hexane). A separate scintillation vial was filled with the phosphonate monomer and solvent. OPF coupons were laid out onto a new, clean glass slide. The edge of the hydrogel was gently dabbed with a KIMWIPE® tissue to remove excess water. The OPF hydrogel was immersed into the solution of Ti(iso-PrO)$_4$/solvent and gently swirled to prevent the sample from sticking to the glass walls and to ensure even exposure of the sample surface. The OPF sample was removed and briefly rinsed in iso-propanol and then placed on a pre-heated glass slide atop a hot plate at 35 to 40° C. in order complete cross-linking of the TiO$_2$ adhesion layer. After heating, the TiO$_2$ coated OPF sample was submerged into the phosphonate monomer solution. The vial containing the system was swirled to prevent sticking, and if needed, tweezers were used to prevent the sample from folding on itself. After the chosen time period had elapsed, the sample was rinsed in iso-propanol and then placed on a pre-heated glass slide atop a hot plate. The surface treated OPF was stored in PBS solution. See Tables 1 to 3, below, for method parameters.

TABLE 1

Optimized Parameters for TiO$_2$/SAMP Modification

| Hydrogel | $t_{Ti(iso-PrO)4}$ (min) | $t_{ODPA}$ (min) | 35° C. | [Ti] Xylene | [ODPA*] Xylene |
|---|---|---|---|---|---|
| Blocks | 1:15 | 240 | 3:00 | 16.8 mM | 1.4 mM |
| Squares | 1:00 | 60 | 1:00 | 16.8 mM | 1.4 mM |
| Ridged | 1:00 | 60 | 1:00 | 16.8 mM | 1.4 mM |

*ODPA is octadecylphosphonic acid

TABLE 2

Parameters for Making Superhydrophobic TiO$_2$/SAMP Surfaces

| Hydrogel | $t_{Ti(iso-PrO)4}$ (min) | $t_{ODPA}$ (min) | 35° C. | [Ti] Xylene | [ODPA*] Xylene |
|---|---|---|---|---|---|
| Blocks | 1:15 | Overnight | 3:30 | 33.2 mM | 1.4 mM |
| Squares | 1:00 | 60 | 1:00 | 16.8 mM | 1.4 mM |
| Ridged | 1:00 | 60 | 1:00 | 16.8 mM | 1.4 mM |

*ODPA is octadecylphosphonic acid

TABLE 3

Adhesion Layer Formation Using Ti(iso-PrO)$_4$: Observations

| solvent | 100 μL/5 mL | 50 μL/5 mL | 25/5 | 25/10 | 10/10 | 5 μL/10 mL |
|---|---|---|---|---|---|---|
| Hexane | Forms thick and uneven coat | Opaque, quickest formation | Opaque | Mildly Opaque | Faintly Opaque | Not Observed |
| Toluene | Forms thick and uneven coat | Opaque | Opaque | Mildly Opaque | Faintly Opaque | Not Observed |
| Xylene | Forms thick and uneven coat | Opaque | Opaque | Mildly Opaque | Faintly Opaque | Not Observed |

Example 2

Cell Studies

NIH 3T3 fibroblast cells were plated on the treated hydrogel surfaces at 50,000 cells per well for 7 days. Both $TiO_2/(1,4$-diphosphono)butane and $TiO_2/(1,12$-diphosphono)dodecane were prepared as surface modifications for the cell studies. See FIG. 2.

Example 3

Deboss-Patterning of OPF

Preparing the materials: OPF was cut into 5 mm×5 mm squares and hydrated with water to form 1 cm×1 cm hydrated OPF squares; this swelling of the OPF is due to the uptake of water. In a typical example, a 20 mL glass vial is used, and glass slides that are used in the debossing process were cut into 1 cm×3.5 cm rectangles; these were rinsed with deionized water and then dried under a stream of nitrogen. Shadow masks were prepared by laser-cutting stripes in sheets of KAPTON® polyimide film (DuPont); masks consisting of ablated stripes about 30 μm wide that were separated by unablated KAPTON® stripes 30 μm wide were typically used. KAPTON® masks used ranged from 10 μm to 120 μm, and were preferably 20 μm to 50 μm thick. The weight used for debossing had a flat bottom to ensure even weight distribution, and ranged from none to 500 grams, and was preferably 100-200 grams.

Preparing the solutions to synthesize the cell-adhesive patterns on OPF: A nitrogen atmosphere bag (alternatively a glove box) was set up as a working space to prepare solutions of two reagents in the 20 mL glass vials. A nitrogen atmosphere box or bag was used to maintain low moisture levels in the preparation of the two types solutions described herein; the first solution prepares the precursor of the oxide adhesion layer, and the second solution is of the phosphonic acid that yields the cell-adhesive surface. The titanium(IV) iso-propoxide solution was prepared from 30 μL of titanium (IV) iso-propoxide (CAS: 546-88-9) that was added to 5 mL of a hydrophobic solvent such as anhydrous toluene (CAS: 108-88-3). When zirconium (IV) iso-propoxide was used instead of the titanium analog, 1 mg of zirconium (IV) iso-propoxide (CAS: 14717-56-7) was added to 5 mL of anhydrous toluene. In a separate vial, 1 mg of 1,12-dodecanediphosphonic acid (CAS: 7450-59-1) was added to 5 mL of anhydrous toluene. These solutions were capped tightly and used in the patterning steps.

Debossing the OPF to prepare cell-adhesive patterns on its surface: A piece of hydrated OPF was dried on filter paper. A small drop of water was placed on a glass slide of dimensions given above, and the OPF coupon was placed on the drop of water to hold it to the glass slide. Any excess water was blotted from the OPF surface using a piece of filter paper. The laser-ablated KAPTON® shadow mask was placed onto the OPF such that the striped area was directly in contact with the OPF surface. The OPF-mask composite was heated to 30° C. on a temperature controlled hot plate, and the mask was depressed into the OPF (debossing) using a 200-gram weight; heating with the mask in place was continued for 15 s. Any excess water was blotted off the surface of the OPF-mask ensemble; the ensemble was then placed into the vial of either the titanium or zirconium precursor solution described above. The ensemble was left immersed for 30 s. The ensemble was then removed from this solution, rinsed 3 times with toluene and then was heated to 30° C. for 30 s; this creates a layer of cross-linked oxide that is patterned on the OPF surface as only the regions of the OPF that are not covered by the KAPTON® shadow mask (the ablated stripes) are exposed to the solution of the titanium or zirconium alkoxide. The ensemble was removed from heat and allowed to cool for 15 s before being immersed in the phosphonic acid solution described above, which yields the cell adhesive stripes on the oxide covered areas of the OPF surface. The ensemble remained in this solution for several hours, and was then rinsed successively with toluene, iso-propanol and water. The KAPTON® mask and glass slide were separated mechanically from the OPF surface if they had not already detached during the rinsing process. The piece of now-patterned OPF was heated on a temperature-controlled hot plate at 30° C. for 30 s. Freshly prepared patterned OPF samples were stored either in water or PBS.

Cleaning reusable materials: The shadow masks were cleaned by sonicating in a low concentration solution of potassium hydroxide for 15 seconds. The shadow masks were then sonicated three more times in water for 5 min each before they were air dried.

Example 4

FFT Analysis on OPF

Routine FFT analyses of cell and matrix alignment on patterned OPF were performed with ImageJ or Fiji software using built-in FFT functions and the "oval profile" plug-in that relate FFT values as intensities as a function of angle with regard to the patterned direction, and are displayed in a circle on the generated image/map. These values were then plotted into a graph form using graphing software such as Microsoft Excel; the orientation direction of the FFT obtained in this way is 90° rotated from the direction of the pattern. In particular, cell or matrix images were cropped to a perfect square, generally 1024 pixels×1024 pixels (682.67 μm×682.67 μm). Image contrast was normalized and enhanced to 0.4% saturation using the built-in function of the software. An FFT analysis was carried out on the image using the built-in FFT function of the software. The generated gray-scale plot was colorized using the Spectrum function. A circle was generated using the "circle mode" software feature around the center where the image color was most intense. Readings at different angles within the circle were evaluated in an output list. The output graph generated is a list of FFTs measured as intensity as a function of angle around the circle generated above. This list can be copied into Microsoft Excel or other graphing software or applications to be plotted into a line graph. The graph values were normalized. Data for FIG. 3 is summarized in the table below.

TABLE 4

Fast Fourier Transform (FFT) analysis of FIG. 3

| Cell culture time | OPF/Ti SAMP pattern | | OPF/Zr SAMP pattern | |
| --- | --- | --- | --- | --- |
| | 30 × 30 μm stripe | unpatterned | 30 × 30 μm stripe | unpatterned |
| Day 1 | 0.50 | 0.94 | 0.54 | 0.98 |
| Day 5 | 0.60 | 0.95 | 0.54 | 0.96 |

Example 5

In Vivo Testing

A 1 cm×1 cm coupon of patterned hydrated OPF is plated with fibroblasts, which are allowed to spread and proliferate in register with the patterned surface. The cell-assembled matrix is decellularized using published methods. A section of this material (about 5 mm×5 mm) is cut from the coupon, rolled and inserted into the transected spinal cord of a rat. The rat is maintained in an approved facility for about 14 weeks, when nerve regeneration is examined by well-known physiological and cytometric methods such as the Basso-Beattie-Breshnahan scale.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the present claims.

All publications cited herein are incorporated by reference in their entirety for all purposes.

What is claimed is:

1. A coated hydrogel comprising an inorganic oxide adhesion layer bonded to the surface of an at least partially hydrated, biocompatible, cross-linked hydrophilic polymer hydrogel, wherein said inorganic oxide is selected from the group consisting of the oxides of Ti, Zr, Al, Mg, Si, Zn, Mo, Nb, Ta, Sn, W, and V, and said hydrogel contains at least 10 nmol of water/cm$^2$ at the surface or available to the surface of the hydrogel.

2. The coated hydrogel of claim 1, wherein said adhesion layer comprises a pattern over at least part of the hydrogel surface.

3. The coated hydrogel of claim 2, wherein said pattern comprises continuous stripes spanning at least part of the hydrogel surface.

4. The coated hydrogel of claim 1, wherein said biocompatible hydrophilic polymer is a cross-linkable polymer selected from the group consisting of polyethylene glycol, polyacrylate, and polyvinyl alcohol.

5. The coated hydrogel of claim 1, wherein said biocompatible hydrophilic polymer is a polysaccharide or polysaccharide derivative selected from the group consisting of polysaccharides, alginates, hyaluronic acids, guar gum, xanthan gum, carrageenan, methyl cellulose, carboxymethyl cellulose, ethyl methyl cellulose, hydroxypropyl cellulose, and hypromellose.

6. The coated hydrogel of claim 4, wherein said cross-linkable polymers are cross-linked with fumarate.

7. The coated hydrogel of claim 4, wherein said biocompatible cross-linked hydrophilic polymer is oligo(polyethylene glycol) fumarate (OPF).

8. The coated hydrogel of claim 1, further comprising a self-assembled monolayer (SAM) bonded to said inorganic oxide adhesion layer, wherein said SAM is selected from organic compounds comprising a phosphonic, carboxylic, sulfonic, phosphinic, phosphoric, sulfinic, or hydroxamic group.

9. The coated hydrogel of claim 8, wherein said SAM comprises a self-assembled monolayer of phosphonates (SAMP).

10. The coated hydrogel of claim 9, wherein said phosphonates are selected from the group consisting of hydrophobic phosphonates and cell-adhesive phosphonates.

11. The coated hydrogel of claim 10, wherein said hydrophobic and cell-adhesive phosphonates are selected from the group consisting of phosphonic acids of structure wherein the R group is selected from the group consisting of optionally substituted alkyl, optionally substituted heteroalkyl, optionally substituted alkenyl, optionally substituted heteroalkenyl, optionally substituted alkynyl, optionally substituted heteroalkynyl, optionally substituted aryl, optionally substituted arylalkyl, optionally substituted heteroaryl, and optionally substituted heteroarylalkyl, where heteroalkyl, heteroalkenyl, heteroalkynyl, heteroaryl and heteroarylalkyl contain one or more heteroatoms selected from the group consisting of O, N and S.

12. The coated hydrogel of claim 11, wherein said hydrophobic phosphonates are selected from the group consisting of R=C$_3$-C$_{30}$ alkyl, and said cell-adhesive phosphonates are selected from the group consisting of R=C$_3$-C$_{30}$ alkyl substituted with a further phosphonate group.

13. The coated hydrogel of claim 12, wherein said cell-adhesive phosphonates are selected from the group consisting of C$_3$-C$_{30}$ α,ω-diphosphonates.

14. A construct for regenerative medicine comprising the coated hydrogel of claim 9.

15. The construct of claim 14, further comprising cells attached to the coated surface of said hydrogel, wherein said cells are selected from the group consisting of fibroblasts, endothelial cells, keratinocytes, osteoblasts, chondroblasts, chondrocytes, hepatocytes, macrophages, cardiac muscle cells, smooth muscle cells, skeletal muscle cells, tendon cells, ligament cells, epithelial cells, stem cells, neural cells, PC12 cells, neural support cells, Schwann cells, radial glial cells, cells that form neurospheres, neural tumor cells, glioblastoma cells and neuroblastoma cells.

16. The construct of claim 15, further comprising an extracellular matrix (ECM).

17. The construct of claim 16, which is decelluarized to leave the ECM attached to said construct.

* * * * *